United States Patent
Ralston et al.

(10) Patent No.: US 6,389,454 B1
(45) Date of Patent: May 14, 2002

(54) MULTI-FACILITY APPOINTMENT SCHEDULING SYSTEM

(75) Inventors: Stephen M. Ralston, Kissimmee; Debra Deahl Valentine, St. Cloud; Michael B. Jenkins, Orlando; Richard S. Couchman, Orlando; Gail R. Couchman, Orlando, all of FL (US)

(73) Assignee: Medical Specialty Software, Kissimee, FL (US)

( * ) Notice: Subject to any disclaimer, the term of this patent is extended or adjusted under 35 U.S.C. 154(b) by 0 days.

(21) Appl. No.: 09/311,095

(22) Filed: May 13, 1999

(51) Int. Cl.⁷ .......................... G06F 15/16; G06F 17/60
(52) U.S. Cl. ................................ 709/204; 705/8
(58) Field of Search .................... 709/204, 203, 709/219; 705/8, 9, 2, 3, 6, 7

(56) References Cited

U.S. PATENT DOCUMENTS

| | | | |
|---|---|---|---|
| 4,937,743 A | 6/1990 | Rassman et al. | 364/401 |
| 5,065,315 A | 11/1991 | Garcia | 364/413.01 |
| 5,113,380 A | 5/1992 | Levine | 368/10 |
| 5,289,531 A | 2/1994 | Levine | 379/93 |
| 5,301,105 A | 4/1994 | Cummings, Jr. | 364/401 |
| 5,321,605 A | 6/1994 | Chapman et al. | 364/402 |
| 5,469,353 A | 11/1995 | Pinsky et al. | 364/413.01 |
| 5,748,907 A | 5/1998 | Crane | 395/202 |
| 5,842,173 A | 11/1998 | Strum et al. | 705/1 |
| 5,848,403 A | 12/1998 | Gabriner et al. | 706/13 |
| 6,101,480 A | * 8/2000 | Conmy et al. | 705/9 |
| 6,104,788 A | * 8/2000 | Schaffer et al. | 379/93.17 |
| 6,112,182 A | * 8/2000 | Akers et al. | 705/21 |

* cited by examiner

Primary Examiner—Dung C. Dinh
Assistant Examiner—Tod Kupstas
(74) Attorney, Agent, or Firm—Lott & Friedland, P.A.

(57) ABSTRACT

A computer-implemented method of scheduling an appointment at a plurality of facilities providing a plurality of services, comprising receiving a packet of client information from a client, the client information including personal data, service data, client appointment preference data, and payment data; comparing the service data to a set of service constraints in order to determine any limitations on the scheduling of the appointment; inputting the client information into a scheduling server; verifying the client information; generating a predetermined number of appointment candidates based upon an analysis of the client information and the appointment scheduling limitations; communicating the appointment candidates to the client; generating an appointment based upon the client's selection of one of the appointment candidates; generating appointment information related to the appointment, the appointment information including the client information, the service constraints, an appointment date, an appointment time, the identity of the available facility, and the resources to be utilized; reporting at least a portion of the appointment information to the client and all of the client information to the available facility; and confirming the appointment in the scheduling server. A data processing system for scheduling an appointment from among a plurality of facilities is also disclosed.

4 Claims, 3 Drawing Sheets

US 6,389,454 B1

MULTI-FACILITY APPOINTMENT SCHEDULING SYSTEM

FIELD OF INVENTION

The present invention relates generally to scheduling systems, and more particularly, the present invention relates to a multi-facility appointment scheduling system whose implementation and manipulation are handled over global, wide-area, or local-area communications networks.

BACKGROUND OF THE INVENTION

In many service-related industries, there exists a need to accommodate the schedules of clients who wish to utilize a plurality of services at a multitude of facilities. For instance, in the medical industry, specialization of practices has led to the development of service providers who serve their clients at a variety of locations, one of which may serve as the provider's central location, or headquarters. For example, a patient (the client), upon the prescription from a physician, may require a procedure to be performed at a specialized facility equipped with specialized equipment. These facilities may either be stand-alone centers or hospitals and service large populations and a great number of physicians. Current methods of scheduling this procedure require a phone conversation with a scheduler at the facility which will provide the service. Since the service could potentially be performed at a variety of sites, the current method could require numerous attempts to contact a variety of facilities before scheduling an appointment at a facility which has the resources (i.e., specific equipment) necessary to provide the service at a time which accommodates the client's scheduling needs. Given the jumbling of locations, services offered at each location, and variables such as specific practitioners' specialties or client preferences, scheduling each location's resources for maximum effectiveness can prove to be burdensome, particularly given the vast amount of data associated with each client's appointment, including personal and medical histories and insurance and other payment information. The services rendered are performed offsite from the client location, in large part because the costs associated with the equipment necessary to perform such services are so high that individual practitioners ordinarily cannot afford such equipment.

Previous attempts have been made to provide systems through which the scheduling of remote locations may be achieved. For example, U.S. Pat. No. 5,848,403 to Gabriner et al. (the '403 patent) describes a genetic algorithm scheduling system which includes a system of encoding and testing hard constraint information. The general scheduling system has information about the scheduling problem, in the form of the resources available for performing tasks, a description of the tasks to be performed, and information about the problem domain.

U.S. Pat. No. 5,842,173 to Strum et al. (the '173 patent) describes a computer-based surgical services management system for communicating between sites of a surgical services facility. The system includes repeaters, remote access via modems, data archives, reactive and predictive scheduling, analysis, data maintenance, telephone communications. U.S. Pat. No. 5,748,907 to Crane (the '907 patent) describes a real-time medical facility management system. U.S. Pat. No. 5,469,353 to Pinsky et al. (the '353 patent) describes a network for providing medical interpretations of radiological images on a national or regional basis. U.S. Pat. No. 5,321,605 to Chapman et al (the '605 patent) describes a system for managing process flow information related to a multiplicity of interrelated organizational tasks.

U.S. Pat. No. 5,289,531 to Levine (the '531 patent) describes an electronic rescheduler for promptly and efficiently rescheduling appointments in a two-part procedure. The first step includes the selection of one or more time periods during which a new appointment would be desired, and in the second step a new appointment is chosen from the selected time periods. The system is telephonically-driven. U.S. Pat. No. 5,301,105 to Cummings, Jr. (the '105 patent) describes a health care management system. U.S. Pat. No. 5,113,380 to Levine (the '380 patent) describes an electronic rescheduler. U.S. Pat. No. 5,065,315 to Garcia (the '315 patent) describes a hospital computerized system for entering information pertinent to a patient's stay in the hospital. U.S. Pat. No. 4,937,743 to Rassman et al. (the '743 patent) describes a method and system for the prospective scheduling, monitoring and management of resources using a computer system.

None of the foregoing systems, each of which is incorporated herein by reference, provides a system which utilizes technology offering access to each of the remote locations via a global communications network such as the Internet.

None of the foregoing systems provides an efficient system for managing the scheduling of multiple facilities, each of which facilities includes multiple resources for providing a variety of client services, such as different procedures to be performed upon clients, each of which procedures requires a specific type of equipment maintained within particular resources of particular facilities.

Consequently, there is a need in the art for a computer implemented multi-facility scheduling system which enables a remote scheduler to arrange client appointments for a variety of services to be provided at a variety of facilities in an efficient, cost-effective manner.

There is a further need in the art for a multi-facility scheduling system to permit a client, or a person acting on the client's behalf, to obtain a variety of scheduling options in order to effectively and efficiently schedule appointments available at a variety of locations.

There is a further need in the art for a multi-facility scheduling system which can also be manipulated on a facility-by-facility basis, with interaction among the various facilities via an electronic communications mechanism such as, for example, the global communications network known as the Internet.

SUMMARY OF THE INVENTION

The present invention solves significant problems in the art by providing a computer-implemented system for scheduling appointments at a plurality of facilities, each facility including a plurality of areas equipped to provide services.

Generally described, the present invention provides a computer-implemented method of scheduling an appointment at a plurality of facilities providing a plurality of services, comprising receiving a packet of client information from a client, the client information including personal data, service data, client appointment preference data, and payment data; comparing the service data to a set of service constraints in order to determine any limitations on the scheduling of the appointment; inputting the client information into a scheduling server; verifying the client information; generating a predetermined number of appointment candidates based upon an analysis of the client information and the appointment scheduling limitations; communicating the appointment candidates to the client; generating an appointment based upon the client's selection of one of the appointment candidates; generating appointment information related to the appointment, the appointment information including the client information, the service constraints, an appointment date, an appointment time, the identity of the available facility, and the resources to be utilized; reporting at least a portion of the appointment information to the client and all of the client information to the available facility; and confirming the appointment in the scheduling server.

In a preferred embodiment, the present invention also comprises a data processing system for scheduling an appointment at a plurality of facilities providing a plurality of services, comprising a receiver for receiving a packet of client information from a client, the client information including personal data, service data, client appointment preference data, and payment data; a constraint determiner for comparing the service data to a set of service constraints in order to determine any limitations on the scheduling of the appointment; an inputter for inputting the client information into a scheduling server; a verifier for verifying the client information; a candidate generator for generating a predetermined number of appointment candidates based upon an analysis of the client information and the appointment scheduling limitations; a candidate communicator for communicating the appointment candidates to the client; an appointment generator for generating an appointment based upon the client's selection of one of the appointment candidates; an appointment information generator for generating appointment information related to the appointment, the appointment information including the client information, the service constraints, an appointment date, an appointment time, the identity of the available facility, and the resources to be utilized; an appointment information reporter for reporting at least a portion of the appointment information to the client and all of the client information to the available facility; and an appointment confirmer for confirming the appointment in the scheduling server.

In an alternative embodiment of the present invention, the method further includes the step of allowing appointments to be rescheduled or canceled, and the data processing system includes an appointment modifier for rescheduling or canceling appointments.

In an alternative embodiment of the present invention, the step of receiving the packet of client information is accomplished via the Internet, a local area network, or a wide area network.

Accordingly, it is an object of the present invention to provide a computer-implemented method of scheduling an appointment at a plurality of facilities providing a plurality of services.

It is another object of the present invention to provide a data processing system for scheduling an appointment at a plurality of facilities providing a plurality of services.

These and other objects, features, and advantages of the present invention will become apparent upon reading the following specification when taken in conjunction with the accompanying drawings.

DETAILED DESCRIPTION OF THE PREFERRED EMBODIMENT

Figure 1:
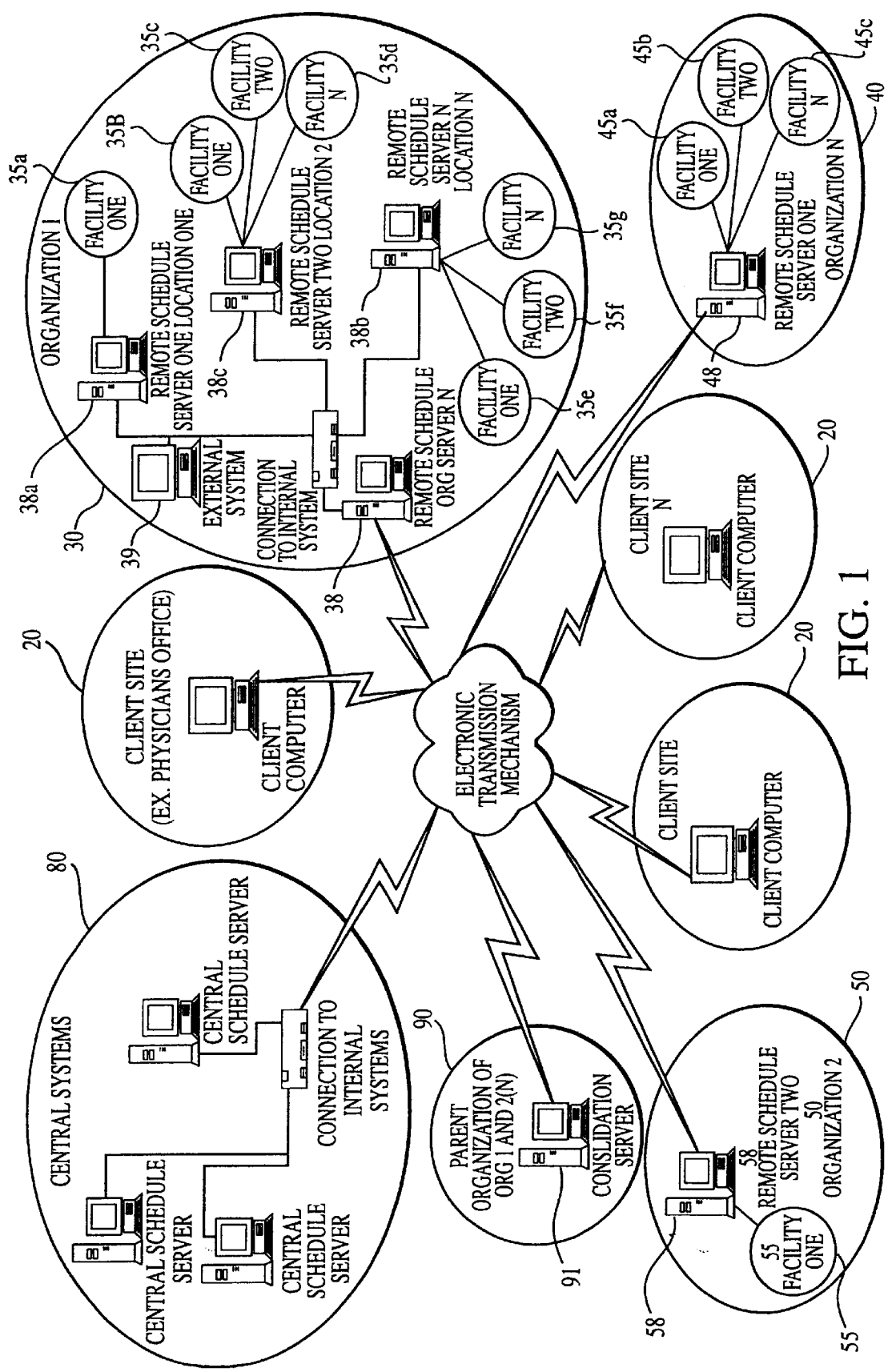
FIG. 1 is a diagrammatic view illustrating the relationship between the clients, the organizations, and the organizations' facilities of the scheduling system of the present invention.
Figure 2:
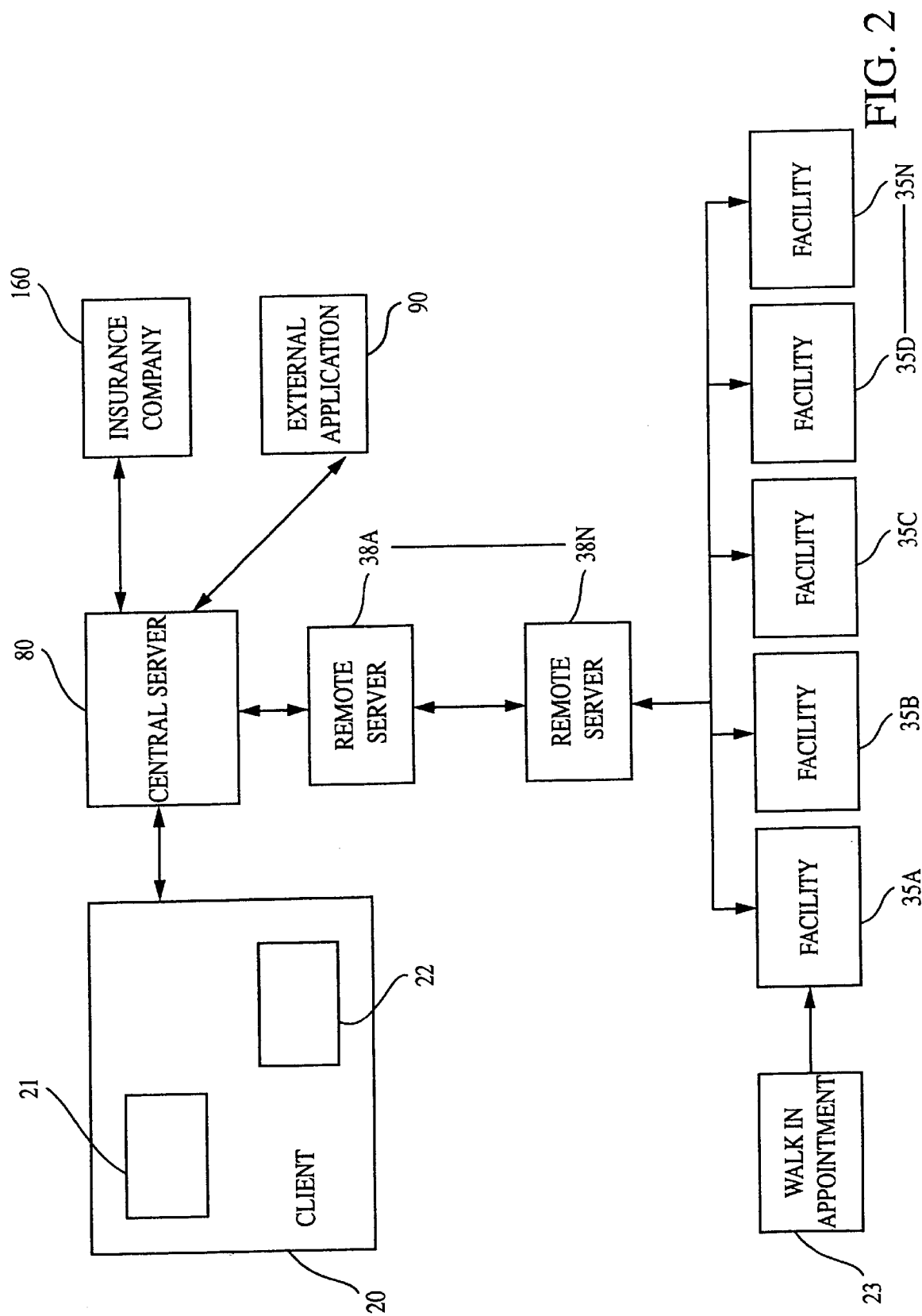
FIG. 2 is an illustration of the flow of information throughout the scheduling system of the present invention, from the initial contact by a client or client's representative through the transmission of appointment information for integration into an application program such as a billing program.

Referring initially to FIG. 1 of the drawings, in which like numerals indicate like elements throughout the several views, in a preferred embodiment the scheduling system 10 of the present invention allows a client 20 to contact, via computer implementation, any one of an organization's 30, 40, 50 multiple facilities 35, 45, 55 to schedule an appointment. A facility is a physical site, such as a clinic, diagnostic center, or treatment center. Referring to FIG. 2, a client 20 may either be the client himself 21 or the client's representative 22, such as in the case of a referring physician seeking a specific type of medical treatment for one of his patients.

An organization 30, 40, 50 is the service provider whose multiple facilities 35, 45, 55 are accessible using the computer-implemented scheduling system 10 of the present invention. Each organization 30, 40, 50 may group its facilities 35, 45, 55, using remote scheduling servers 38, 48, 58, so as to permit access to each facility's 35, 45, 55 schedules. For instance, facility 35a is independently connected to a scheduling server 38a, while facilities 35b, 35c, and 35d are collectively connected to a scheduling server 38b. The distinction between these types of groupings is that the server 38a connected to facility 35a can only access scheduling information for facility 35a, while the server 38b connected to facilities 35b, 35c, 35d can access all three of these facilities' scheduling information. The scheduling information maintained on the various servers 38, 48, 58 is accessible via an electronic communications link 70 between the servers and, for example, a global communications network such as the Internet.

Access to each organization's 30, 40, 50 collective scheduling information begins at the scheduling system's 10 central schedule servers 80. When the client 20 wishes to schedule an appointment for a specific type of treatment, the client 20 connects to the scheduling system 10 by connecting to one of the central schedule servers 80 via the electronic transmission mechanism 70, which network may take the form of the Internet, a local area network (LAN), wide area network (WAN) or even a telephone call. The client 20, by entering a predetermined access code, is able to access an organization's facilities. Once the client 20 accesses a specific organization, the scheduling system 10 prompts the client 20 to provide client information for the purpose of scheduling an appointment.

Client information includes personal data about the client, such as the client's name, date of birth, social security number, address, telephone number, referring physician, and the like; service data, such as the diagnosis and recommended treatments; payment data, such as the client's insurance information; and client appointment preference data, such as the preferred date, time, and specific facility where the client would like to schedule an appointment. The scheduling system confirms the information received from the client with the client and verifies certain of the information, such as for instance the client's insurance information (as depicted in FIG. 2 at reference number 160), by communicating, via means familiar to those of ordinary skill in the relevant art, with sources of such information, such as the insurance company.

Once the scheduling system 10 receives the packet of client information from the client 20, it compares the service data to an existing set of service constraints in order to determine any constraints on the scheduling of an appointment for the client. For instance, if a client 20 wishes to schedule a Magnetic Resonance Imaging (MRI) treatment, the MRI may not be capable of administration if the client, for example, wears metal braces on his teeth. Also, it is common for certain procedures to be ordered at the same time. Those procedures are specified and named as a procedure group. A procedure group can consist of procedures of one or more modalities. Certain procedures must be performed on the same day, while others must not be performed on the same day. Constraints for a procedure specify which procedures must be performed on the same day, and which must not be performed on the same day. Additionally, certain procedures must be performed in a specific sequence. Precedence rules defined for a procedure specify the required sequence of certain procedures.

Once the central scheduling server 80 generates the appointment scheduling limitations, the limitations and the client appointment preferences are utilized in order to generate a predetermined number of appointment candidates. The central scheduling server 80 communicates the requests to the remote schedule servers 38, 48, 58, which actually generate the candidates and pass them back to the central server 80. Each remote schedule server 38, 48, 58 generates appointment candidates using data from the particular facilities 35, 45, 55 to which each remote server 38, 48, 58 has access. Thus, the scheduling server 80 generates the appointment candidates by communicating with the organization's remote schedule servers 38, 48, 58, which in turn communicate with the organization's facilities 35, 45, 55 to determine which of the facilities are available to provide the requisite services at the preferred date and time. The availability and downtime of the facility and resources is considered during the scheduling process. The operating hours of the facility, suites and equipment, and the working hours of the staff contribute to the determination of availability. Restrictions for a procedure and procedure group also contribute to the determination of availability. A scheduling restriction at a particular date and time, such as preventive maintenance or a staff meeting, is defined as downtime. Availability masks are specified to define when an entity is available. An availability mask consists of the start time, frequency, day of week, and duration. For example, for a facility with operating hours of 9 am to 7 pm Monday through Friday, and 9 am to 12 pm on Saturday, a mask is created for each weekday beginning at 9 am for 10 hours, and one for Saturday beginning at 9 am for 3 hours. A duration is defined for each procedure. Therefore, the scheduling process considers the following issues when attempting to schedule an appointment:

Resources required by procedures in the schedule group

Availability masks defined for the facility

Availability masks defined for the resources required by procedures in the schedule group Availability masks defined for the procedures, procedure groups and modalities in the schedule group Existing appointments for the resources required by the procedures in the schedule group Availability of the patient The facilities 35, 45, 55 communicate their availability back to the central scheduling server 80 via their respective remote schedule servers 38, 48, 58. The scheduling server 80 then communicates the various appointment candidates directly to the client 20. If the client 20 wishes to select one of the appointment candidates, the client 20 so notifies the scheduling server 80. If the client does not want to select any of the appointment candidates, an alternative set of appointment candidates is generated in the same manner as the initial set of candidates. Upon receipt of the client's notification as to which appointment candidate the client wishes to select, the scheduling server 80 communicates the notification to the selected facility 35, 45, 55, via the facility's remote schedule server 38, 48, 58. The scheduling system 10 then generates information related to the selected appointment, including the client information, the service constraints, the appointment date and time, the facility at which the appointment will occur, and the specific resources to be utilized at the facility during the appointment. Resources include the specific room to be utilized for the appointment, along with the staff and equipment required to perform a procedure. Staff denotes the technical, professional, or administrative staff whom are represented within the facility. Equipment denotes the types of machinery or apparatus located within the facility. The scheduling system 10 then reports all of the appointment information to the facility 35, 45, 55 at which the service will be performed, and a portion of this information—the client information, the appointment date and time, and the facility's identity— to the client 20, and confirms the appointment with the facility 35, 45, 55 at which the appointment is scheduled to occur. In connection with the scheduling of the appointment, a unique appointment number is transmitted to both the client 20 and the facility 35, 45, 55 at which the appointment is scheduled.

The scheduling system 10 of the present invention also includes the capability of handling the rescheduling or canceling of previously-scheduled appointments. A client 20 may connect to the scheduling server 80 via the method discussed above and, once connected, may notify the scheduling server 80 of his appointment number, at which time the scheduling server 80 will locate the appointment information generated when the appointment was scheduled. Once the appointment information is retrieved, the scheduling server 80 will provide the client 20 with options regarding the appointment, including without limitation confirmation, cancellation, and modification. If the client 20 wishes to cancel the appointment, the scheduling server 80 will notify the facility 35, 45, 55 at which the appointment is scheduled to occur, in order that the facility 35, 45, 55 can remove whatever restrictions were placed upon it, in terms of resources, by the scheduling of the appointment, thus freeing up those resources for a different client's use. Should the client 20 wish to reschedule the appointment, the scheduling server 80 will obtain from the client 20 a new set of client appointment preference data and will, in the same manner described above, generate a new set of appointment candidates from which the client 20 may select in order to reschedule his appointment.

As illustrated in FIG. 2, the scheduling system 10 of the present invention is also capable of allocating facilities and resources to clients who seek and/or receive services without an appointment, i.e., walk-in clients 23, and of reallocating facilities and resources in situations where clients with scheduled appointments to not appear for their appointments without canceling their appointments. When such situations occur, personnel at the facility 35, 45, 55 affected by the walk-in or no-show enter into the facility's remote schedule server 38, 48, 58 appropriate information pertaining to the resources encumbered (in the case of a walk-in) or available (in the case of a no-show), and this information is in turn transmitted via the electronics communications network 70 to the central scheduling server 80.

Looking at FIG. 2, once the appointment is generated and confirmed with the client 20, the appointment information can also be made available for export to an external system 90, such as a billing program. For example, once the appointment is generated, the client information, including insurance information, can be integrated into an organization's billing program so that the client 20 is appropriately billed for the services rendered at the facility 35, 45, 55 at the time of the appointment.

Figure 3:
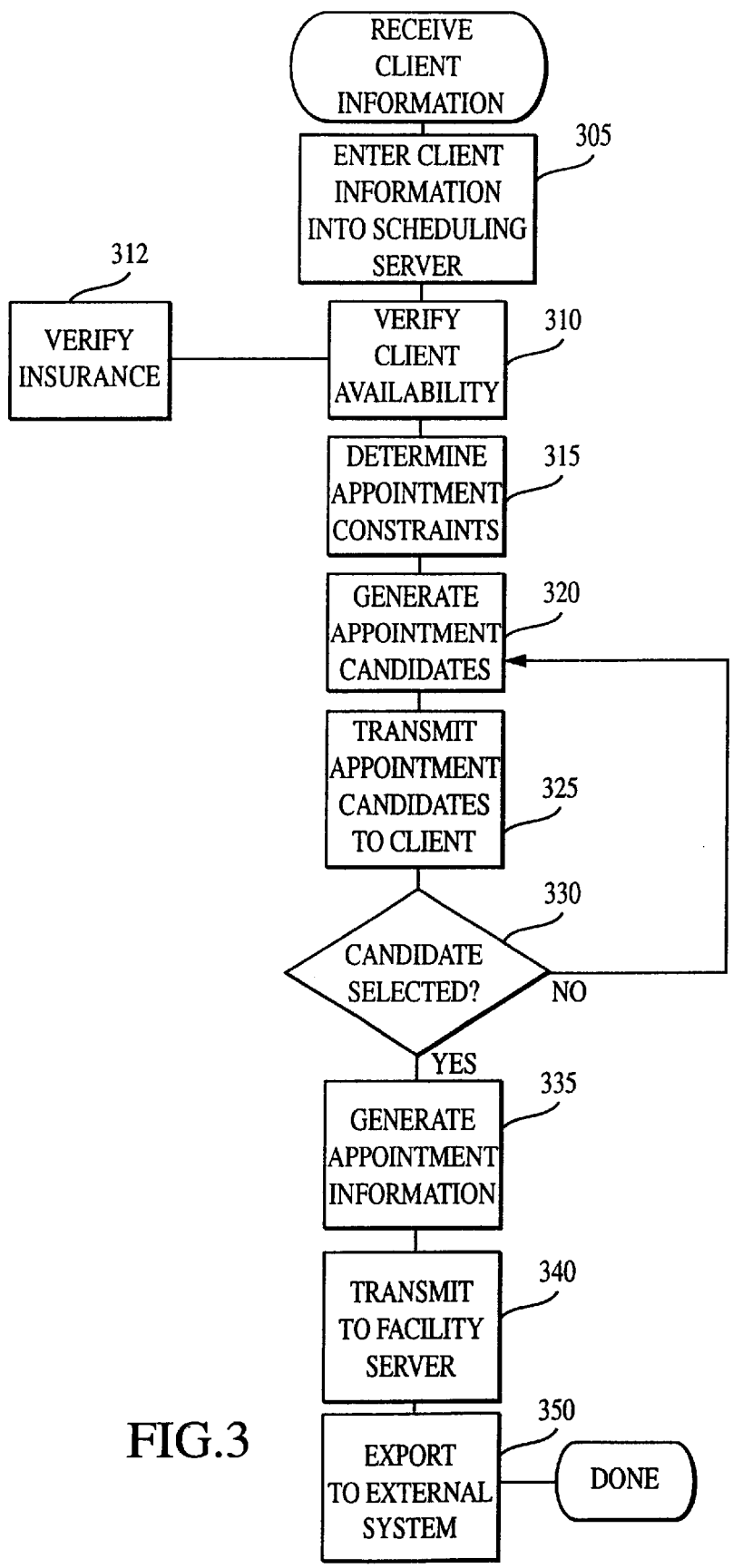
FIG. 3 is a flow chart illustrating the method of the preferred embodiment of the present invention.

FIG. 3 is a flow chart illustrating a typical operation of the 1o scheduling system of the present invention. In steps 305–315, the appointment candidates are generated. Once steps 305, 310, 312, and 315 occur, and the system generates a set of appointment candidates, steps 320, 325, and 330 repeatedly determine if the client has selected an appointment candidate. In step 335, once the client selects an appointment candidate, the appointment information is generated, and in step 340, the appointment information is transmitted, as discussed above, to the client and facility. In step 350, the appointment information is transmitted to the external system 90 for integration into another application.

In an alternative embodiment of the scheduling system of the present invention, the client 20 can access multiple organizations 30, 40, 50 for the purpose of scheduling appointments at any of the multiple organizations' multiple facilities 35, 45, 55. For example, one organization 30 may consist of 7 facilities and a second organization 40 may consist of 3 different facilities. Under the alternative embodiment of the present invention, the client 20, either directly 21 or through his representative 22, may access scheduling information from both organizations and therefore schedule an appointment based upon the availability of up to ten (10) different facilities. Under such a scenario, the various organizations'30, 40, 50 scheduling information is compiled in a consolidation server 60.

While the foregoing description relates to an application of the present invention in the medical industry, it should be understood that the present invention is applicable to any industry in which the scheduling of resources at a variety of locations is desired, such as, for example, the hotel industry (reserving guest rooms or meeting areas among various hotels in a chain) or convention industry (reserving meeting areas within a geographic area hosting a particular convention).

Accordingly, it will be understood that the preferred embodiment of the present invention has been disclosed by way of example and that other modifications and alterations may occur to those skilled in the art without departing from the scope and spirit of the appended claims.

What is claimed is:

1. A computer implemented method of scheduling an appointment at a plurality of facilities providing a plurality of services, comprising:

receiving a packet of client information from a client, said client information including personal data, service data, client appointment preference data, and payment data;

comparing said service data to a set of service constraints in order to determine any limitation on the scheduling of said appointment;

inputting said client information into a scheduling server;

verifying said client information;

generating a predetermined number of appointment candidates from said plurality of facilities based upon an analysis of said client information and said appointment scheduling limitations;

communicating said appointment candidates to said client;

generating an appointment based upon said client's selection of one of said appointment candidates;

generating appointment information related to said appointment, said appointment information including said client information, said service constraints, an appointment date, an appointment time, the identity of the available facility, and the resources to be utilized;

reporting at least a portion of said appointment information to said client and all of said client information to said available facility; and confirming said appointment in said scheduling server.

2. The method of claim 1, wherein said client information is received via an electronic transmission mechanism.

3. A data processing system for scheduling an appointment at a plurality of facilities providing a plurality of services, comprising:

receiving means for receiving a packet of client information from a client, said client information including personal data, service data, client appointment preference data, and payment data;

comparing means for comparing said service data to a set of service constraints in order to determine any limitation on the scheduling of said appointment;

inputting means for inputting said client information into a scheduling server;

verifying means for verifying said client information;

candidate generating means for generating a predetermined number of appointment candidates from said plurality of facilities based upon an analysis of said client information and said appointment scheduling limitations;

communicating means for communicating said appointment candidates to said client;

appointment generating means for generating an appointment based upon said client's selection of one of said appointment candidates;

information generating means for generating appointment information related to said appointment, said appointment information including said client information, said service constraints, an appointment date, an appointment time, the identity of the available facility, and the resources to be utilized;

reporting means for reporting at least a portion of said appointment information to said client and all of said client information to said available facility; and confirming means for confirming said appointment in said scheduling server.

4. A data processing system for scheduling an appointment at a plurality of facilities providing a plurality of services, comprising:

a receiver for receiving a packet of client information from a client, said client information including personal data, service data, client appointment preference data, and payment data;

a constraint determiner for comparing said service data to a set of service constraints in order to determine any limitation on the scheduling of said appointment;

an inputter for inputting said client information into a scheduling server;

a verifier for verifying said client information;

a candidate generator for generating a predetermined number of appointment candidates from said plurality of facilities based upon an analysis of said client information and said appointment scheduling limitations;

a candidate communicator for communicating said appointment candidates to said client;

an appointment generator for generating an appointment based upon said client's selection of one of said appointment candidates;

an appointment information generator for generating appointment information related to said appointment, said appointment information including said client information, said service constraints, an appointment date, an appointment time, the identity of the available facility, and the resources to be utilized;

an appointment information reporter for reporting at least a portion of said appointment information to said client and all of said client information to said available facility; and an appointment confirmer for confirming said appointment in said scheduling server.

* * * * *